US011737926B2

(12) United States Patent
Astilla et al.

(10) Patent No.: US 11,737,926 B2
(45) Date of Patent: Aug. 29, 2023

(54) APPARATUS AND METHOD FOR SUSPENDING A RESIDUUM PROTECTION DEVICE

(71) Applicant: Limbguard, LLC, Durham, NC (US)

(72) Inventors: Michael Joseph Astilla, Durham, NC (US); Laura Brewer Riedel, Durham, NC (US)

(73) Assignee: Limbguard, LLC, Durham, NC (US)

( * ) Notice: Subject to any disclaimer, the term of this patent is extended or adjusted under 35 U.S.C. 154(b) by 574 days.

(21) Appl. No.: 16/654,848

(22) Filed: Oct. 16, 2019

(65) Prior Publication Data
US 2021/0113385 A1 Apr. 22, 2021

(51) Int. Cl.
*A61F 13/06* (2006.01)
*A61F 13/00* (2006.01)

(52) U.S. Cl.
CPC .... *A61F 13/062* (2013.01); *A61F 2013/0028* (2013.01); *A61F 2013/00093* (2013.01); *A61F 2013/00272* (2013.01)

(58) Field of Classification Search
CPC .. A61F 2/50; A61F 2/78; A61F 2/7812; A61F 2/80; A61F 2002/7818; A61F 2002/785; A61F 5/00; A61F 5/01; A61F 5/0102; A61F 5/0106; A61F 5/0109; A61F 5/0123; A61F 13/06; A61F 13/061; A61F 13/062; A61F 15/008; A61F 2005/0197; A61F 15/006; A61F 2/7843; A61F 5/0111
See application file for complete search history.

(56) References Cited

U.S. PATENT DOCUMENTS

| 3,827,107 A * | 8/1974 | Moore | A61F 15/006 128/DIG. 15 |
| 3,889,301 A * | 6/1975 | Bonner, Sr. | A61F 2/7843 623/37 |
| 4,446,856 A * | 5/1984 | Jordan | A61F 5/0111 602/27 |
| 2005/0059919 A1* | 3/2005 | Farraday | A61F 2/80 623/36 |

(Continued)

OTHER PUBLICATIONS

Laprade, Robert, "Femoral Condyle Articular Cartilage Injury", [Online], [retrieved Sep. 12, 2022]; retrieved from website entitled Robert Laprade MD, PHD; using internet URL:https://drrobertlaprademd.com/femoral-condyle-articular-cartilage-injury-oats-treatment-minneapolis-st-paul-edina-eagan-mn/ (Year: 2022).*

*Primary Examiner* — Ophelia A Hawthorne
*Assistant Examiner* — Gina McCarthy
(74) *Attorney, Agent, or Firm* — Taylor English Duma LLP

(57) ABSTRACT

An apparatus suspends a post-amputation residuum protection device for a below the knee amputation. The suspending apparatus comprises an elongated arcuate first shell defining an open interior channel. The first shell is adapted to receive at least a portion of the residuum and the residuum protection device into the interior channel. A flexible second shell includes a circumferential wedge extending radially inwardly from a portion of an inner surface. The second shell is configured to be received within the first shell and adapted to cover the residuum adjacent to the knee. The wedge is adapted to bear against the residuum above the medial femoral condyle such that the wedge is received in the supracondylar space for suspending the residuum protection device.

14 Claims, 9 Drawing Sheets

(56) References Cited

U.S. PATENT DOCUMENTS

| | | | |
|---|---|---|---|
| 2007/0225824 A1* | 9/2007 | Einarsson | A61F 2/80 623/36 |
| 2010/0036505 A1* | 2/2010 | Hassler | A61F 2/78 623/33 |
| 2010/0191348 A1* | 7/2010 | Kettwig | A61F 2/78 623/33 |
| 2012/0209404 A1* | 8/2012 | Astilla | A61F 2/7812 623/33 |
| 2015/0320576 A1 | 11/2015 | Riedel et al. | |

* cited by examiner

APPARATUS AND METHOD FOR SUSPENDING A RESIDUUM PROTECTION DEVICE

BACKGROUND

An apparatus and method are described for suspending and supporting a device for protecting a post-amputation residuum.

Following amputation of a limb, or a portion of a limb, edema often occurs in the body region of the amputation causing volume fluctuations in the amputation residuum. It is important to stabilize the amputation residuum by applying compression to the residuum. Compression may be provided by placing the residuum in a splint or a dedicated post-amputation residuum protection device for minimizing swelling and protecting the residuum. One such device is described and shown in U.S. Pat. No. 8,679,193, the contents of which are hereby incorporated by reference in their entirety. The patented residuum protection device may be used after amputation of a portion of a leg and includes a posterior shell, a pre-tibial shell, optional enclosure panels, and a circular pad. The pre-tibial shell is flexible and movable within the posterior shell for accommodating fluctuations in volume and varying variance of the residuum. The residuum protection device thus stabilizes an amputation residuum while accommodating fluctuations in the volume and the diameter of the residuum.

A post-amputation residuum protection device can require an apparatus for suspending the device to ensure that the device does not migrate away from the residuum. Conventionally, for amputation of a leg or a portion of a leg, a strap suspended from a waist belt has been secured to the residuum protection device. The strap is connected to the device with rivets or screws or via anatomical suspension on the residuum. However, anatomical suspension requires remaking the device as the residuum anatomy changes due to volume fluctuations. As a result, this technique often results in sub-optimal suspension and residuum protection.

For the foregoing reasons, there is a need for an improved apparatus and method for suspending a post-amputation residuum protection device. The improved apparatus and method should effectively secure the residuum protection device while preventing the residuum protection device from migrating away from the residuum.

SUMMARY

An apparatus is provided for suspending a post-amputation residuum protection device for a below the knee amputation. The suspending apparatus comprises an elongated arcuate first shell having a longitudinal axis and defining an open interior channel. The first shell is adapted to receive at least a portion of the residuum and the residuum protection device into the interior channel of the shell. A flexible second shell has an inner surface and an outer surface. The second shell includes a circumferential wedge extending radially inwardly from a portion of the inner surface. The second shell is configured to be received within the first shell and adapted to cover the residuum adjacent to the knee forming a sleeve with first shell for surrounding the residuum and the residuum protection device. The wedge is adapted to bear against the residuum above the medial femoral condyle of the residuum such that the wedge is received in the supracondylar space for suspending the residuum protection device. In one aspect, the first shell is adapted to cover at least a portion of the edges of the second shell for enclosing at least a portion of the length of the residuum within the first shell and the second shell.

In another aspect, the second shell comprises an inner foam layer comprising a soft material, and an outer foam layer comprising a rigid material, wherein the outer foam layer is positioned adjacent to the inner foam layer.

The suspending apparatus may further comprise a strap member secured to the second shell. The strap has a free distal end and includes a buckle at the other end. The strap is adapted to wrap around the first shell and the second shell compressing the shells to a shape conforming to the outside of the combined suspending apparatus and the residuum protection device. Each of the ends of the strap member is configured to wrap in opposite directions around the suspending apparatus, wherein the wrapped ends of the strap are aligned. The suspending apparatus may further comprise a pair of mating fasteners spaced on the outer surface of the free distal end of the strap member for securing the overlapping free distal end of the strap, and the mating fasteners can comprise hook and loop fasteners.

A method is also provided for supracondylar suspension of a post-amputation residuum protection device for a below the knee amputation. The suspension method comprises the steps of providing an elongated arcuate first shell having a longitudinal axis and defining an open interior channel, and placing at least a portion of a residuum and the residuum protection device in the interior channel of the first shell. A second shell is provided having an inner surface and an outer surface, the second shell including a circumferential wedge extending radially inwardly from a portion of the inner surface. The second shell is placed within the first shell to cover at least a portion of the residuum wherein a portion of each edge of the first shell defining the opening partially overlaps the edges of the second shell forming a sleeve around the residuum with the residuum protection device. The wedge is positioned in the supracondylar space for suspending the residuum protection device.

In one aspect, the suspension method may further comprise the step of providing a strap member secured to the second shell, and wrapping the ends of the strap in opposite directions around the around the first shell and the second shell and fastening the overlapping ends together for compressing the shells to a shape conforming to the outside of the combined suspending apparatus and the residuum protection device.

In another embodiment, an apparatus is provided for post-amputation residuum maintenance for a below the knee amputation. The apparatus comprises an elongated posterior shell having a longitudinal axis and defining a hollow interior closed at a distal end. The posterior shell has an opening extending from a proximal end and is adapted to receive a residuum into the hollow interior. A pre-tibial shell, having a longitudinal axis and substantially arcuate in a cross-section taken transverse to the longitudinal axis, is adapted to be positioned adjacent to the residuum and configured to cover at least a portion of the opening of the posterior shell. An elongated arcuate first suspension shell has a longitudinal axis and defines an open interior channel. The first suspension shell is adapted to receive at least a portion of the residuum and the residuum protection device into the interior channel. A flexible second suspension shell has an inner surface and an outer surface. The second suspension shell includes a circumferential wedge extending radially inwardly from a portion of the inner surface. The second suspension shell is configured to be received within the first suspension shell and adapted to cover the residuum adjacent to the knee forming a sleeve with first suspension shell for surrounding the residuum and the residuum protection device. The wedge is adapted to bear against the residuum above the medial femoral condyle of the residuum such that the wedge is received in the supracondylar space for suspending the residuum protection device.

In one aspect, the first suspension shell is adapted to cover at least a portion of the edges of the second suspension shell for enclosing at least a portion of the length of the residuum within the first suspension shell and the second suspension shell.

In another aspect, the second suspension shell comprises an inner foam layer comprising a soft material, and an outer foam layer comprising a rigid material, wherein the outer foam layer is positioned adjacent to the inner foam layer.

The apparatus may further comprise a strap member secured to the second suspension shell, the strap having a free distal end, and including a buckle at the other end. The strap is adapted to wrap around the first suspension shell and the second suspension shell compressing the suspension shells to a shape conforming to the outside of the combined suspension shells and the posterior shell. Each of the ends of the strap member can be configured to wrap in opposite directions around the suspension shells and the posterior shell, wherein the wrapped ends of the strap are aligned. The apparatus may further comprise a pair of mating fasteners spaced on the outer surface of the free distal end of the strap member for securing the overlapping free distal end of the strap. The mating fasteners may comprise hook and loop fasteners.

BRIEF DESCRIPTION OF THE DRAWINGS

For a more complete understanding of the present invention, reference should now be had to the embodiments shown in the accompanying drawings and described below. In the drawings.

DESCRIPTION

Certain terminology is used herein for convenience only and is not to be taken as a limitation on the invention. For example, words such as "upper," "lower," "left," "right," "horizontal," "vertical," "upward," and "downward" merely describe the configuration shown in the FIGs. Indeed, the components may be oriented in any direction and the terminology, therefore, should be understood as encompassing such variations unless specified otherwise. Where possible, any terms expressed in the singular form herein are meant to also include the plural form and vice versa, unless explicitly stated otherwise. Like numbers refer to like elements throughout. Throughout this disclosure, where a process or method is shown or described, the steps of the method may be performed in any order or simultaneously, unless it is clear from the context that one step depends on another being performed first.

The term "residuum" as used herein includes the remaining portion of an amputated body part, such as an amputated limb and, in particular, a leg. In one application, as described herein, the leg is amputated below the knee.

It is understood that, although a suspension apparatus and method will be described in detail herein with reference to a particular post-amputation residuum protection device as described in U.S. Pat. No. 8,679,193, the suspension apparatus and method may be applied to, and find utility with, other residuum devices. As described above, there are a number of devices used for post-amputation residuum protection. Therefore, although the present suspending apparatus will be described in detail herein as embodied for use with a particular device, it is not intended to be so limited. The present suspending apparatus and method may be used with other residuum devices. Thus, the suspending apparatus has general applicability to any device providing residuum protection wherein improvements in suspension and ease of use are desired.

Figure 1:
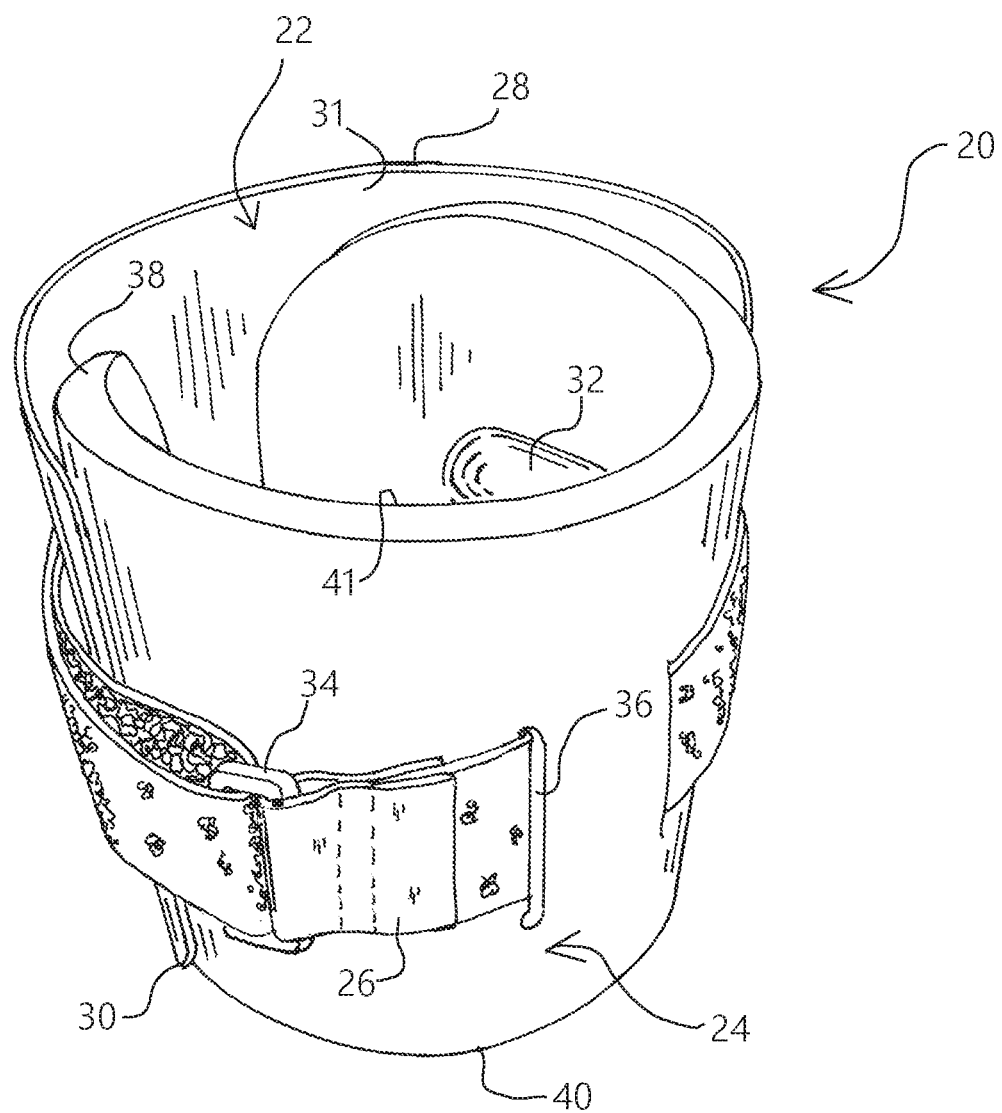
FIG. 1 is a perspective view of an embodiment of an apparatus for suspending a post-amputation residuum device.
Figure 2:
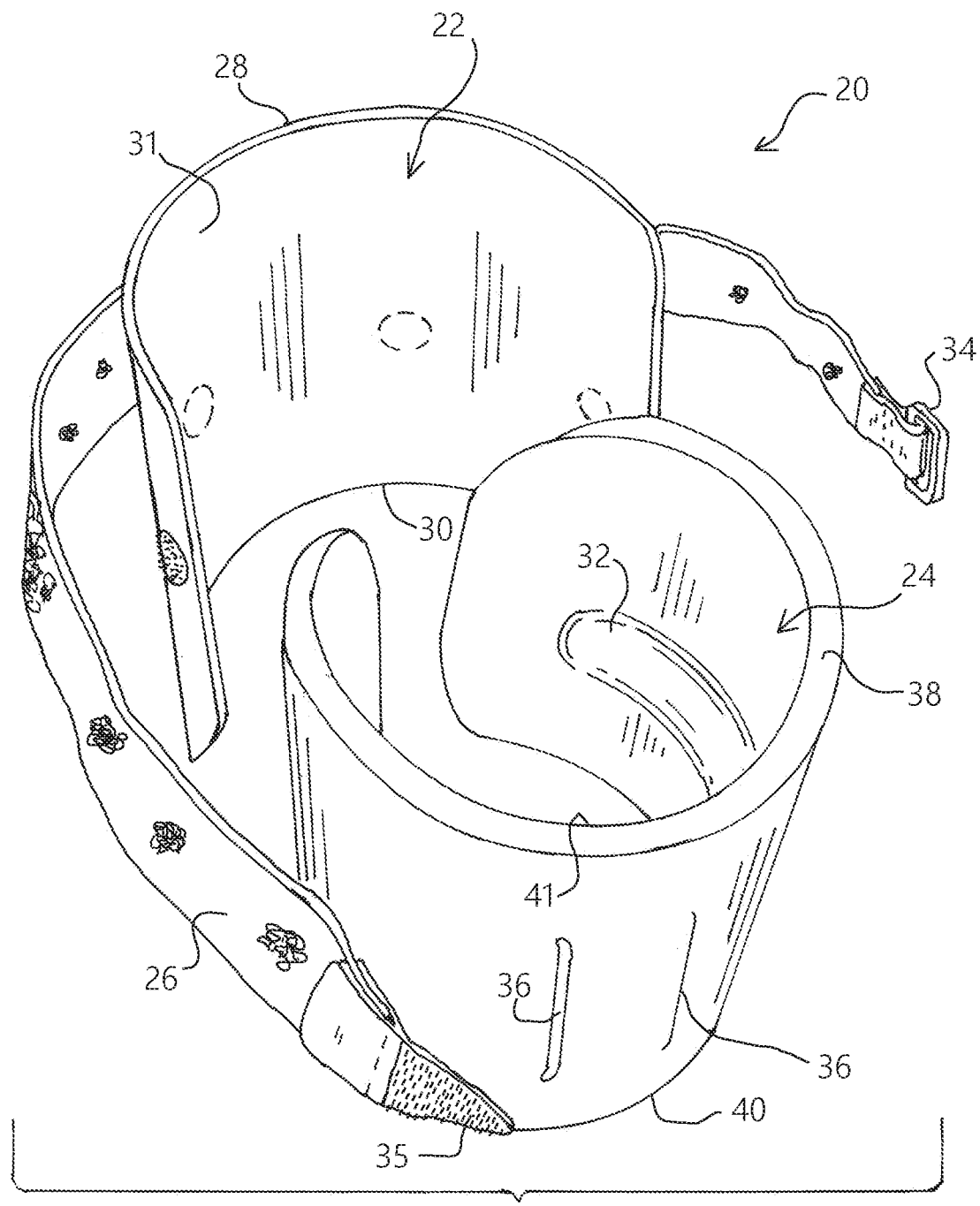
FIG. 2 is an exploded perspective view of the suspending apparatus as shown in FIG. 1.

Referring now to the drawings, wherein like reference numerals designate corresponding or similar elements throughout the several views, an embodiment of an apparatus for suspending a post-amputation residuum protection device is shown in FIGS. 1 and 2 and generally designated at 20. The suspending apparatus 20 comprises a posterior shell 22, an anterior shell 24, and a strap member 26. The posterior shell 22 has a proximal end portion 28 and a distal end portion 30 that are spaced along a longitudinal axis L of the posterior shell 22. The posterior shell 22 is generally c-shaped and open at both ends 28, 30 thereby defining an open interior channel 31 extending longitudinally from the proximal end portion 28 to the distal end portion 30. The posterior shell 22 may have any length and diameter, which may be adjusted to fit the amputation residuum. The posterior shell 22 may also have any thickness and the thickness may vary along the length of the posterior shell. For example, in some embodiments, the proximal end portion 28 of the posterior shell 22 may have a greater thickness than the distal end portion 30.

In some embodiments, the posterior shell 22 is formed from a semi-rigid polymer material that is shaped, in one embodiment, to comfortably accommodate the posterior of a thigh, knee, and trans-tibial residuum following amputation of the leg below the knee. Suitable semi-rigid polymer materials include thermoplastics; polyolefins; plastics; ethylene vinyl acetate, polypropylene, polyethylene, polyethylene terephthalate, styrene, vinyl acetate, acrylonitrile, polyvinyl chloride, polyamide, silicone, rubber, and carbohydrates polymers or copolymers; cross-linked polymers or copolymers; and combinations thereof. The posterior shell 22, in some embodiments, is fabricated by thermo-forming the polymer material over a cylindrical model. In other embodiments, the posterior shell 22 is formed by injection molding. The posterior shell 22 may have any color or opacity. For example, the posterior shell 22 may be clear, slightly opaque, or completely opaque. In the case where the posterior shell 22 is clear or slightly opaque, the position of the anterior shell 24 or any collecting fluids may be visible from the outside of the posterior shell 22. Similarly, anything positioned on the outside of the posterior shell 22, such as fabric fasteners, may be visible from the inside. To enhance the comfort of the user, the inner surface of the posterior shell 22 may be lined. For example, the posterior shell 22 may include padding, wicking material, a gel layer, and the like.

The anterior shell 24 has a proximal end portion 38 and a distal end portion 40 that are spaced along a longitudinal axis L of the anterior shell 24. The anterior shell 24 is generally c-shaped and open at both ends 38, 40 thereby defining an open interior channel 41 extending longitudinally from the proximal end portion 38 to the distal end portion 40.

The anterior shell 24 may comprise an inner foam layer positioned adjacent to an outer foam layer. In some embodiments, the inner foam layer is laminated to the outer foam layer. The layers may be laminated using heat, adhesive, or a combination thereof. The laminated foam layers may then be cut to size, thermo-molded to a generally cylindrical model and, optionally, beveled along one or more edges. Alternatively, the anterior shell 24 is formed through an injection-molding process.

The inner foam layer of the anterior shell 24 may comprise a soft material. The outer foam layer of the anterior shell 24 may comprise a rigid, high density material. This arrangement enhances the comfort and protection of the residuum. The foam used in the anterior shell 24 may be open cell foam, closed cell foam, polymer based foams, plant based foams, or combinations thereof. Examples of the inner foam layer and the outer foam layer include, without limitation, polyolefin, polyether, polyester, polyethylene, polypropylene, ethylene vinyl acetate, rubber, polyimide, vinyl chloride, polyurethane, styrene, carbon, soy, and cellulose based foams, and combinations thereof. The inner foam layer and outer foam layer may further include any number of additives or topical treatments such as antimicrobials, water resistant additives, coloring agents, and the like. Although two foam layers are described, it will be understood that the anterior shell 24 may include only a single layer of foam or any number of layers, including additional foam layers or layers of other materials. For example, the anterior shell 24 may include plastic, gel, fabric, and the like.

The anterior shell 24 is configured to be flexible in order to accommodate the shape of the knee above the amputation. As shown in FIGS. 4-8, the thickness of the anterior shell 24 can vary. In some embodiments, the inner foam layer has a beveled edge, tapering as it extends to the outer side edges of the anterior shell 24. In other embodiments, the inner foam layer may also taper as it extends to the outer edges of the proximal and distal ends 38, 40. It will be understood, however, that the inner foam layer and outer foam layer of the anterior shell 24 may have any thickness as long as the anterior shell 24 fits securely against the amputation residuum. The anterior shell 24 may be modified in any way by the user. For example, the anterior shell 24 may be easily trimmed or cut with scissors to better fit the user's limb.

Referring to FIGS. 4-8, an inner surface 25 of the anterior shell 24 includes an integral wedge 32 for positioning in a bony prominence just above the knee on the inner side of the leg, which is referred to as the medial femoral condyle. The wedge 32 extends radially inwardly from the inner surface 25 of the anterior shell and runs circumferentially along a portion of the inner surface transverse to the longitudinal axis of the anterior shell 24. It is understood that the wedge 32 can also be made as a removable piece or as a part of a removable medial wall in the anterior shell 24.

Figure 3:
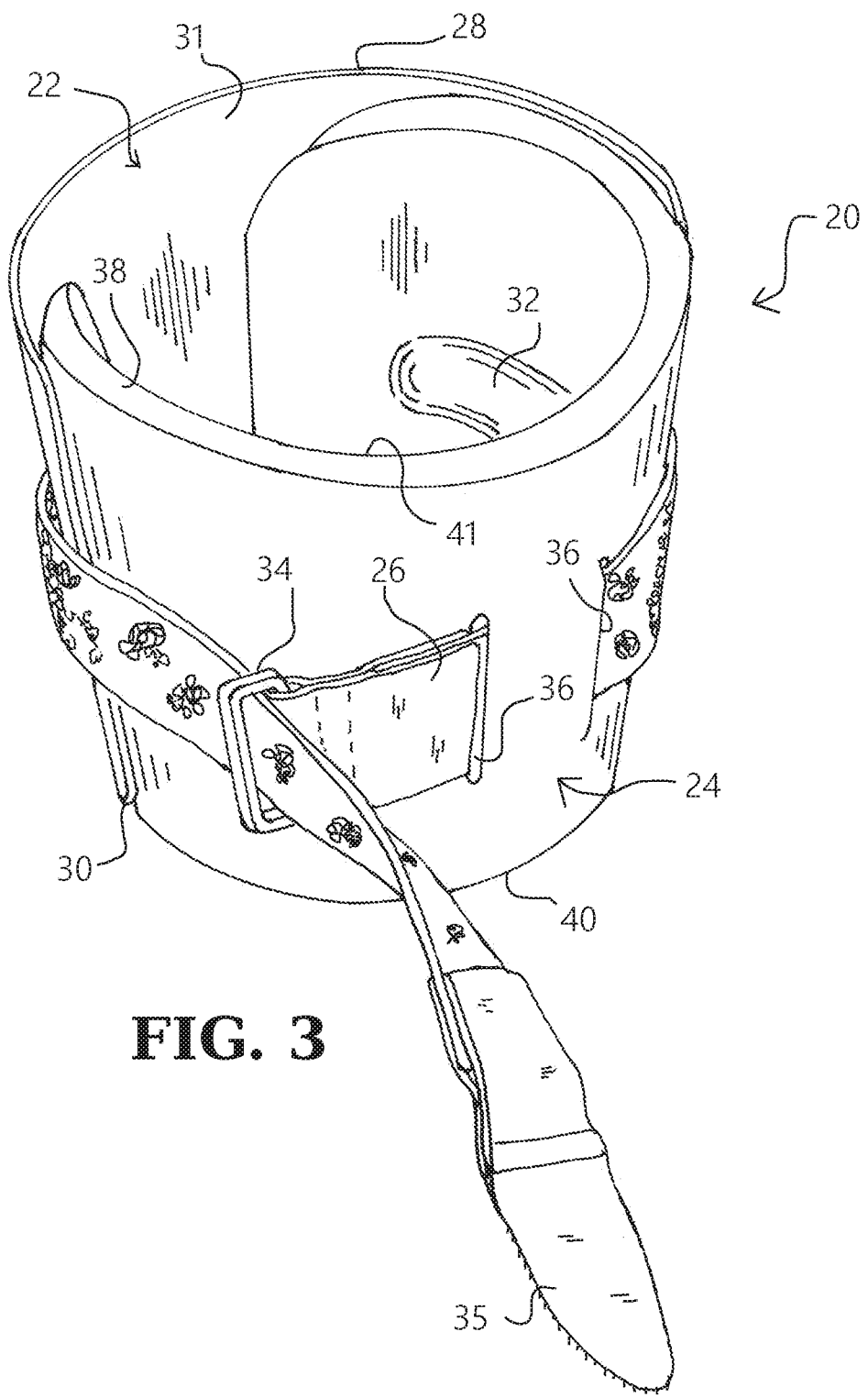
FIG. 3 is a perspective view of the suspending apparatus as shown in FIG. 1 partially assembled having a loose strap.
Figure 4:
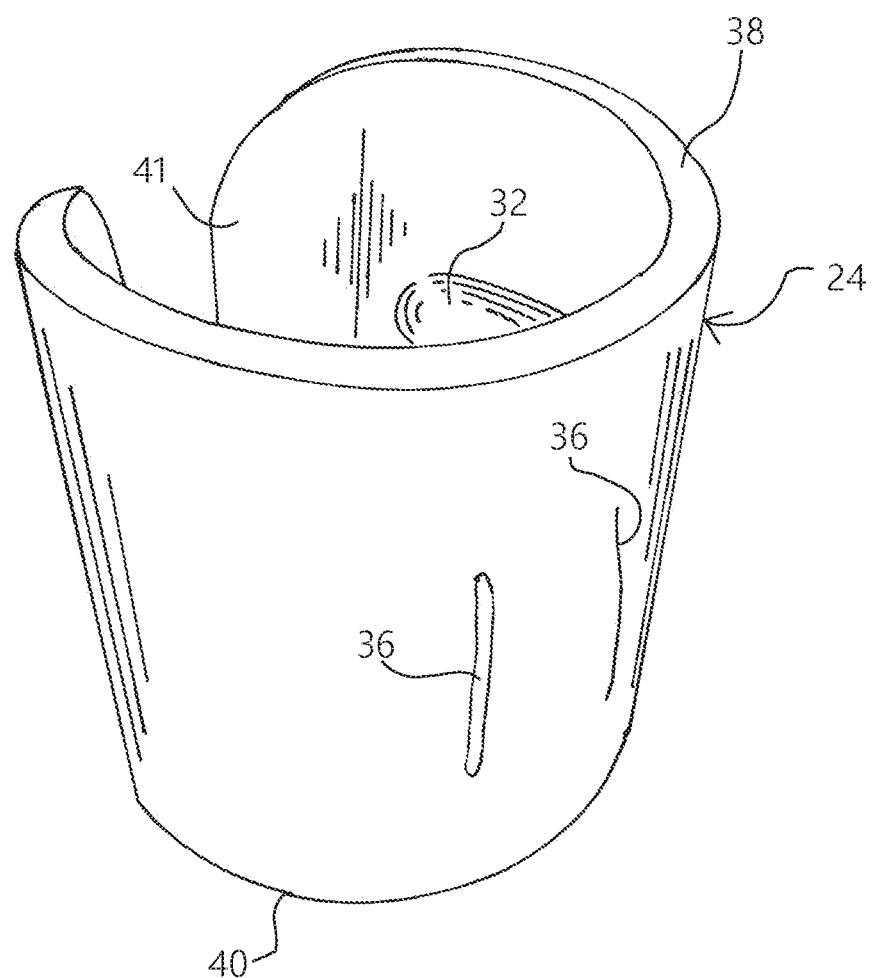
FIG. 4 is a top front perspective view of an embodiment of an anterior shell for use with the suspending apparatus as shown in FIG. 1.
Figure 5:
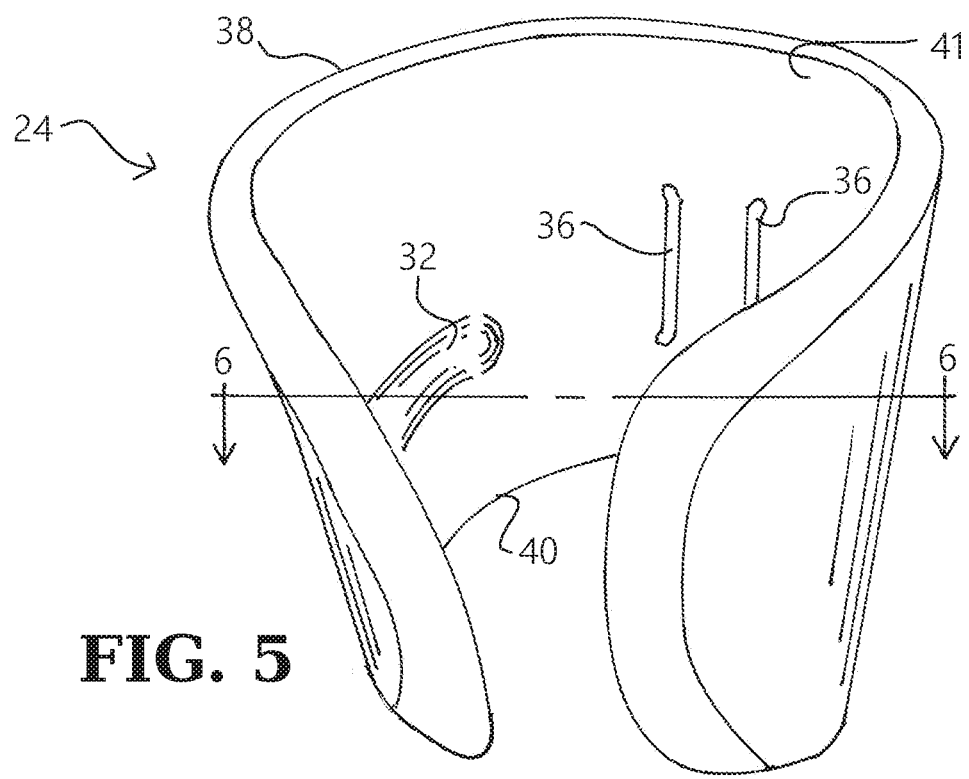
FIG. 5 is a rear perspective view of the anterior shell as shown in FIG. 4.
Figure 6:
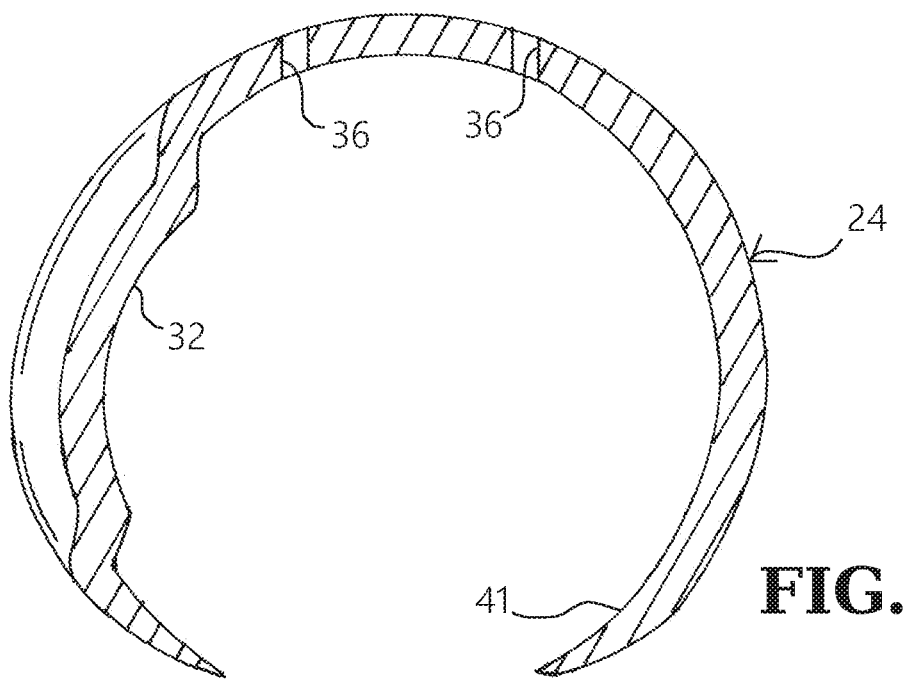
FIG. 6 is a transverse cross-section view of the anterior shell taken along line 6-6 of FIG. 5.
Figure 7:
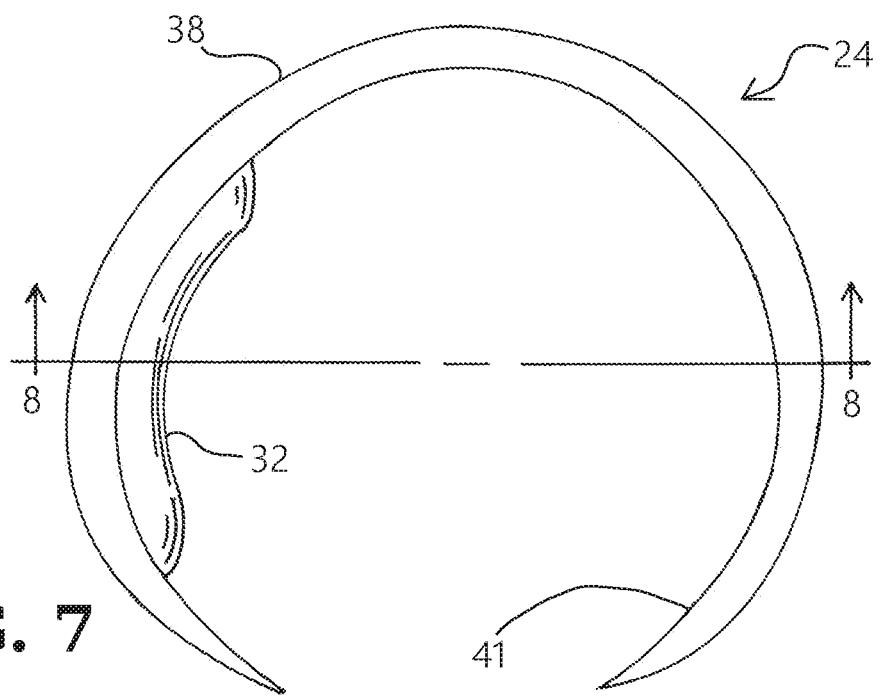
FIG. 7 is a top plan view of the anterior shell as shown in FIG. 4.
Figure 8:
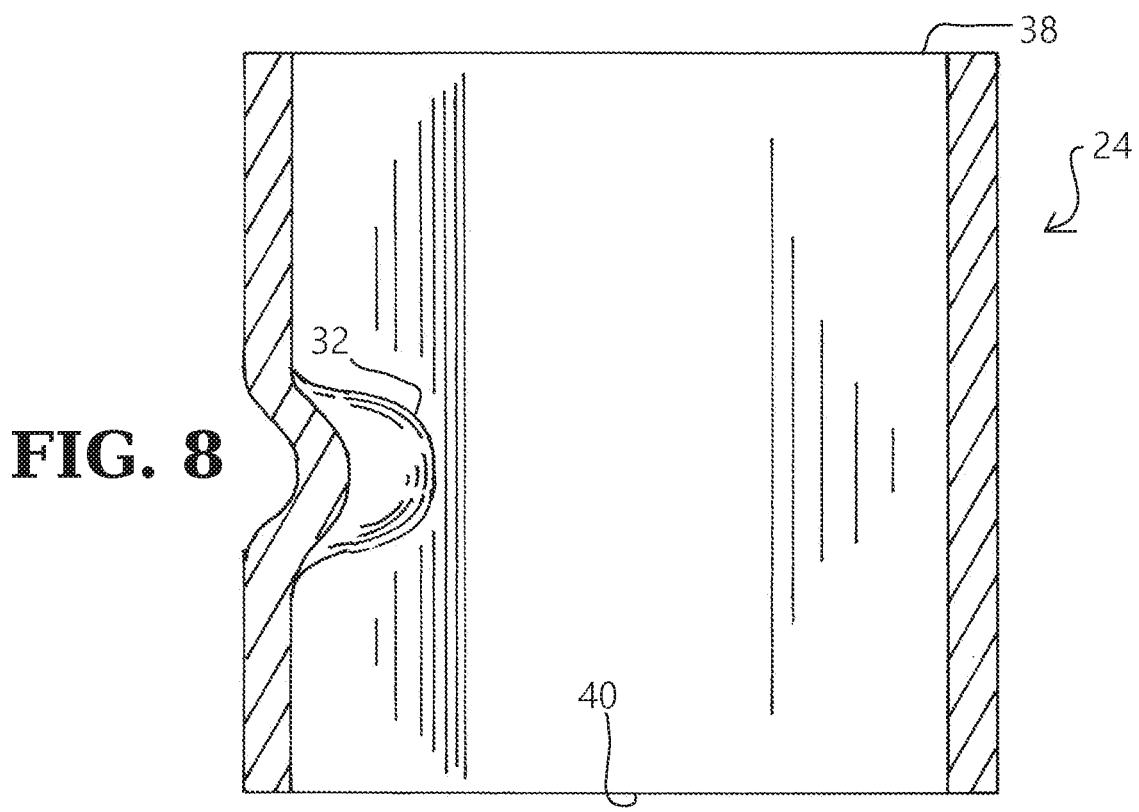
FIG. 8 is a cross-section view of the anterior shell taken along line 8-8 of FIG. 7.

The strap member 26 comprises an elongated fastener having a buckle 34 at one end and a free end 35. The strap 26 is slidingly received in two spaced longitudinal slits 36 in the anterior shell 24 at a midpoint along the longitudinal axis of the anterior shell 24. The strap 26 is configured to encircle a "sleeve" formed by the joined posterior shell 22 and anterior shell 24 enclosing a patient's leg. As shown in FIG. 3, the free end 35 of the strap 26 passes through the buckle 34 and fastens to itself, for example, with fastener strips comprising fabric made of fastening material, such as hook and loop type fasteners (e.g., "Velcro"). This arrangement allows the user to selectively tighten or loosen the tension on the strap 26 to secure the suspending apparatus 20 to the leg and provide support to the residuum protection device. The length of the fastened strap 26 is adjustable so that the pressure with which the suspending apparatus bears against the leg above the bone can be selectively adjusted as required. Alternative configurations to the strap member, including two separate straps, webbed straps, or elastic bands with clips or other connection means are suitable.

Figure 9A:
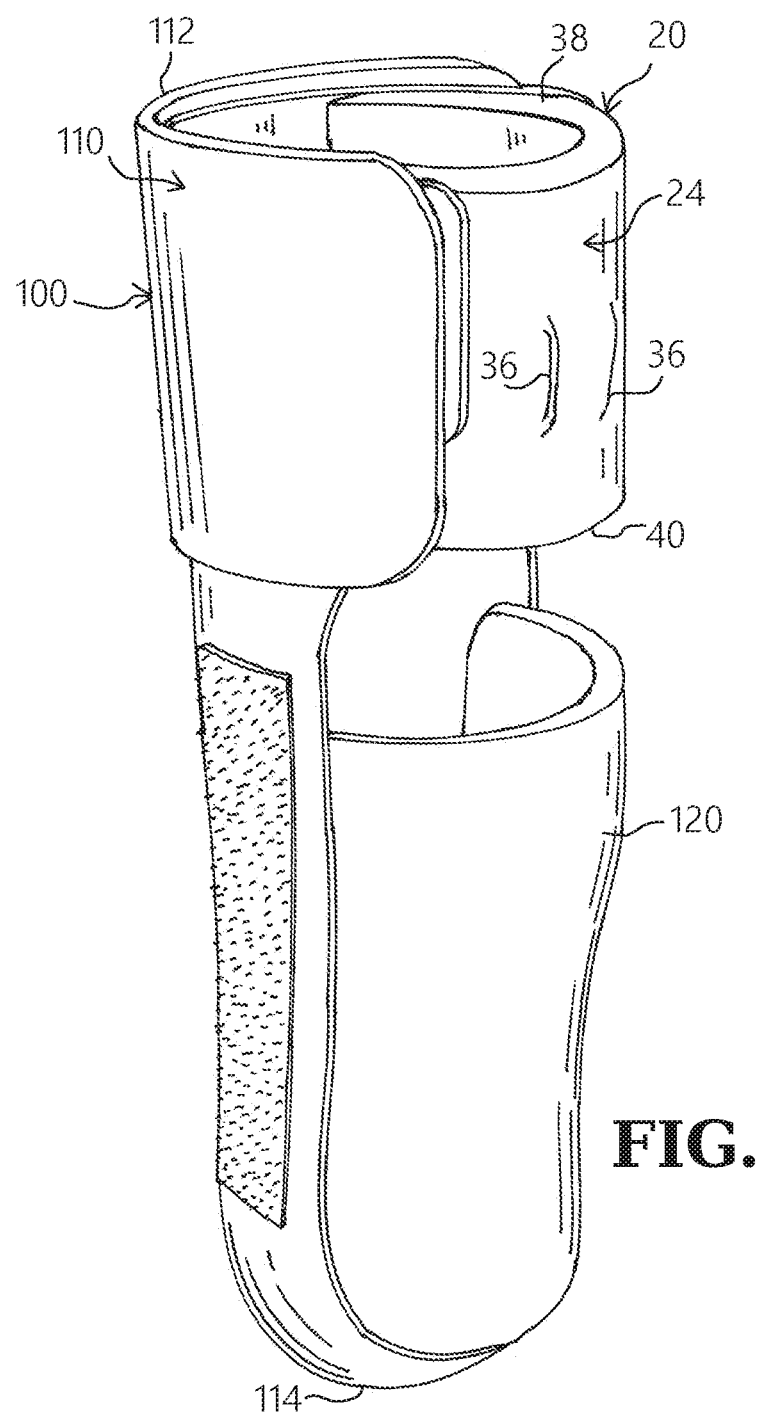
FIG. 9A is a perspective view of a portion of the suspending apparatus as shown in FIG. 1 assembled with parts of an embodiment of a post-amputation residuum protection device.
Figure 9B:
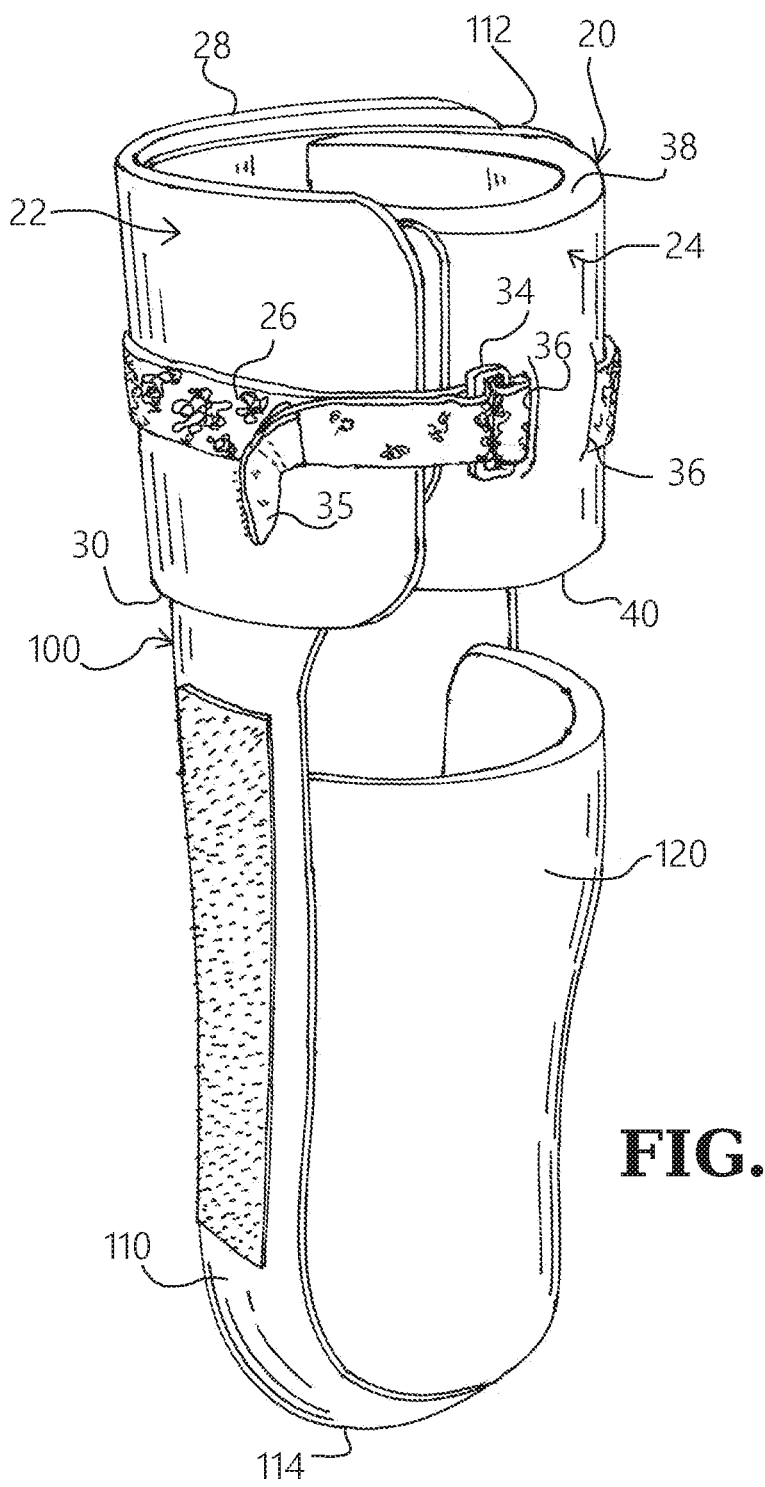
FIG. 9B is a perspective view of the suspending apparatus as shown in FIG. 1 assembled with the parts of the post-amputation residuum protection device as shown in FIG. 9A.
Figure 10:
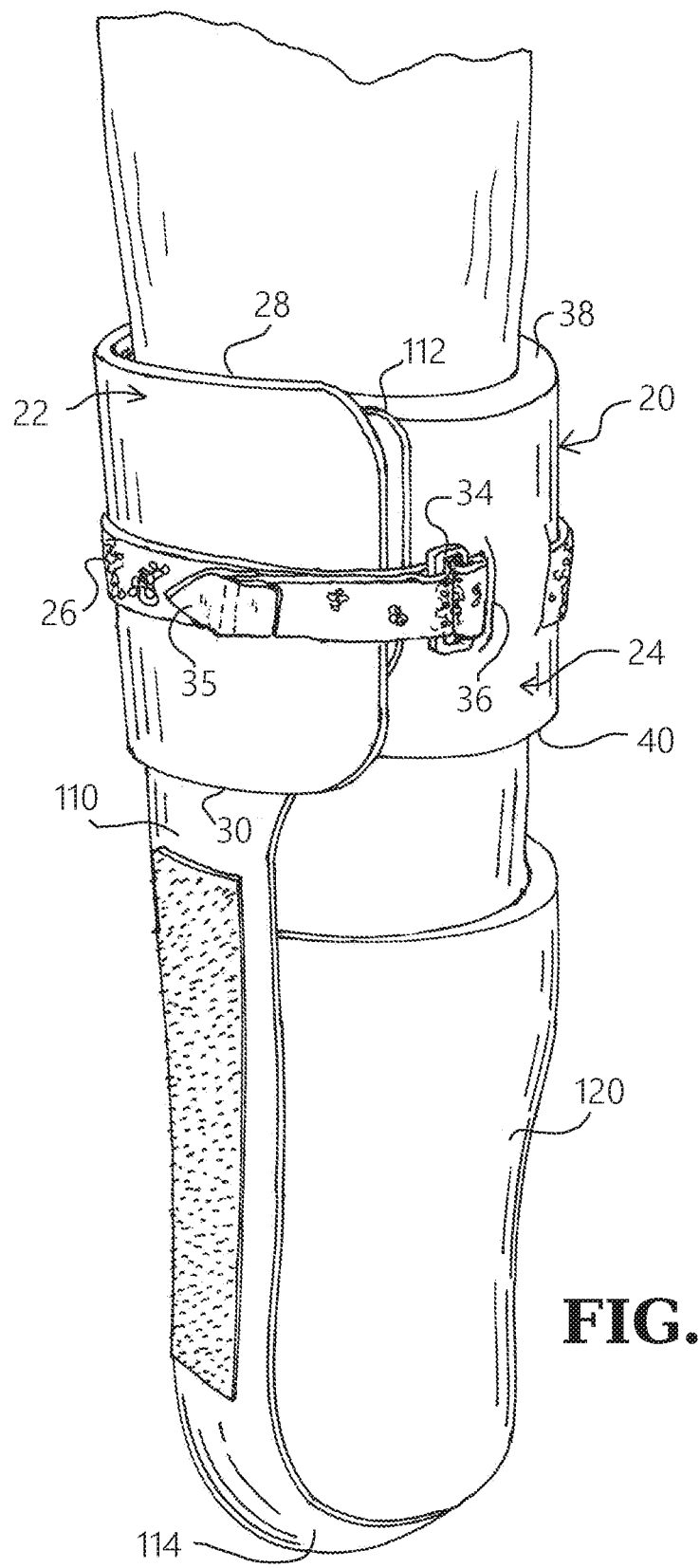
FIG. 10 is a perspective view of the suspending apparatus assembled with the post-amputation residuum protection device showing a portion of a residuum.

In use, a post-amputation residuum protection device, generally designated at 100 in FIGS. 9A-10, is secured to a residuum. The amputation residuum protection device 100 includes a posterior shell 110 and a pre-tibial shell 120. The posterior shell 110 is applied to the posterior of a patient's thigh and residual limb by positioning at least a portion of the residuum into the hollow interior of the posterior shell 110. In some embodiments, a proximal end portion 112 of the posterior shell 110 extends along at least a portion of the user's thigh and a distal end portion 114 extends along at least a portion of the user's tibia. The relative position of the posterior shell 110 to the residuum is such that the distal end of the residuum is received in the closed distal end portion 114 of the residuum device 100. Depending on the length of the amputation residuum, the posterior shell 110 may, for example, be trimmed at the open proximal end 112.

The pre-tibial shell 120 is positioned in the interior of the posterior shell 110 such that the pre-tibial shell 120 comes in contact with the anterior aspect of the amputation residuum. In an application where amputation is below the knee, the pre-tibial shell 120 is positioned such that the distal end of the pre-tibial shell 120 is adjacent the distal end of the residuum and extending upwardly to the patella. The pre-tibial shell 120 is tucked into the posterior shell 110 in order to appropriately accommodate for volume loss secondary to edema reduction within the residuum. In some embodiments, at least a portion of the posterior shell 110 defining the interior overlaps at least a portion of the peripheral edges of the pre-tibial shell 120. This allows the posterior shell 110, when expanding or contracting in response to volume and diameter variances in the amputation residuum, to move relative to the pre-tibial shell 120. When the pre-tibial shell 120 is adjacent to the amputation residuum exposed through the posterior shell 110, the pre-tibial shell 120 floats to accommodate the amputation residuum as it expands and contracts while it simultaneously stabilizes the amputation residuum. In some embodiments, the amputation residuum is enclosed in the interior of the posterior shell 110 by fastening flexible enclosure panels (not shown) over the anterior of the patient's residuum to fastener strips on the posterior shell 110. The residuum is enclosed in the posterior shell 110 by fastening the enclosure panels over the pre-tibial shell 120.

The suspending apparatus 20 may be applied to the post-amputation residuum protection device 100 as shown in FIGS. 9A-10. The anterior shell 24 is positioned in the interior of the proximal end portion 112 of the posterior shell 110 such that the anterior shell 24 comes in contact with the knee region (FIG. 9A). The anterior shell 24 is tucked into the posterior shell 110 in order to appropriately accommodate for volume loss secondary to edema reduction within the residuum. In some embodiments, at least a portion of the posterior shell 110 defining the interior overlaps at least a portion of the peripheral edges of the anterior shell 24, which allows the posterior shell 110 to move relative to the anterior shell 24 when expanding or contracting in response to volume and diameter variances in the amputation residuum. Next, the inner surface of the posterior shell 22 of the suspending apparatus 20 is placed against the back of the residuum and the posterior shell 112 of the residuum protection device 100 (FIGS. 9B and 10). The lower end of the posterior shell 22 extends to just below the knee level. The posterior shell 22 extends around the residuum to the anterior shell 24 such that a sleeve forms, conforming to the outside of the residuum.

In the arrangement shown, the anterior shell 24 is positioned around and partially over medial femoral condyle, which is a bony prominence just above the knee on the inner side of the leg of a patient. The anterior shell 24 is sufficiently flexible to conform to the contour of this portion of the residuum around the knee. In this position, the elongated wedge 32 fits over and bears against the residual limb above the medial femoral condyle. The anterior shell 24 and associated wedge 32 remain in a secured position relative to the medial femoral condyle by means of the strap 26. The user passes the free end 35 of the strap through the buckle 34 and wraps the strap 26 around the joined posterior shell 22 and the anterior shell 24 and around the proximal portion of the residuum protection device partially enveloping the suspending apparatus 20. One or more fastener strips may be positioned on the outer surface of the posterior shell 110. In one embodiment, hook and loop fasteners, such as Velcro, are used to removably attach the strap 26 to the posterior shell 22. Other fasteners may be used as recognized by one of ordinary skill in the art, such as a series of buttons or snaps, or a combination of webbed straps and adjustable clips.

The inner surface of the free end 35 of the strap 26 overlaps the outer surface of the strap and is secured together with fasteners to achieve a snug fit. The secured straps provide compressive resistance to distal migration of the residuum protection device 100. The strap 26 may be used at any time to appropriately adjust the tension for supporting the suspending apparatus 20 with the appropriate tension to ensure proper suspension of the residuum protection device 100. The supracondylar suspension method keeps the residuum protection device 100 on the limb based on the anatomic contours of the residuum. Other types of fastening systems may also be used with the residuum device 100 and suspending apparatus 20, such as clamps, straps, belts, tapes, and the like.

In some embodiments, a kit is provided. The kit comprises one or more residuum protection devices of posterior shells 110, pre-tibial shells 120 and enclosure panels along with at least one suspending apparatus 20. In other embodiments, the kit comprises packaging, a container, instructions, labels, foam padding, a prosthetic sock or prosthetic shrinker, straps, a strapping apparatus, and the like.

The suspending apparatus 20 has many advantages, including helping retain a residuum protection device on the residual limb of a below-the-knee amputee. The suspending apparatus 20 provides a flexible wrap-around design configured to accommodate the size and shape of the residuum and post-amputation residuum protection device and provide a secure and comfortable fit. Due to the flexibility of the anterior shell 24 and to a lesser extent the posterior shell 22, the suspending apparatus 20 need not be custom fit for individual patients as the configuration fits numerous individuals of differing bone structures. Anatomical suspension negates remaking the device as the residuum anatomy changes due to volume fluctuations resulting in consistent, optimal suspension and residuum protection. The wrap around design enhances post amputation protection device suspension and adjustability and allows the patient to wear the residuum protection device without risk of detachment.

Although the suspending apparatus has been shown and described in considerable detail with respect to only a few exemplary embodiments thereof, it should be understood by those skilled in the art that we do not intend to limit the suspending apparatus to the embodiments since various modifications, omissions and additions may be made to the disclosed embodiments without materially departing from the novel teachings and advantages of the suspending apparatus, particularly in light of the foregoing teachings. For example, while the suspending apparatus is described herein for use with a leg, it will be understood that the apparatus may also be used for an arm or other body part. Accordingly, we intend to cover all such modifications, omissions, additions and equivalents as may be included within the spirit and scope of the suspending apparatus as defined by the following claims. In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures.

We claim:

1. An apparatus for suspending a post-amputation residuum protection device for a below the knee amputation leaving a residuum having a medial femoral condyle defining a supracondylar space, the suspending apparatus comprising:

an elongated arcuate first shell having a longitudinal axis and defining a first open interior channel, the first shell adapted to receive at least a portion of the residuum and the residuum protection device into the first open interior channel of the shell; and a flexible second shell having a proximal end, a distal end, an inner surface defining a second open interior channel, and an outer surface, the second shell including a wedge comprising a protrusion extending radially inwardly into the second open interior channel of the second shell from along a portion of the inner surface spaced from the proximal end and the distal end of the second shell, wherein the protrusion is elongated and includes a pair of major side surfaces projecting into the second open interior channel at an angle other than normal with respect to the inner surface of the second shell, the side surfaces joining at a common longitudinal ridge coaxial with a central longitudinal axis of the protrusion and extending partially circumferentially along the inner surface of the second shell, the second shell configured to be received within the first shell and adapted to cover the residuum adjacent to the knee forming a sleeve with the first shell for surrounding the residuum and the residuum protection device, wherein the wedge is adapted to bear against the residuum above the medial femoral condyle of the residuum such that the protrusion is received in the supracondylar space of the medial femoral condyle for suspending the residuum protection device.

2. The suspending apparatus as recited in claim 1, further comprising a strap member secured to the second shell, the strap member having a free distal end, and including a buckle at the other end, wherein the strap member is adapted to wrap around the first shell and the second shell compressing the shells to a shape conforming to an outside surface of the combined suspending apparatus and the residuum protection device.

3. The suspending apparatus as recited in claim 2, wherein each of the ends of the strap member is configured to wrap in opposite directions around the suspending apparatus, wherein the wrapped ends of the strap member are aligned.

4. The suspending apparatus of claim 3, further comprising a pair of mating fasteners spaced on the outer surface of the free distal end of the strap member for securing the free distal end of the strap member in an overlapping manner.

5. The supporting apparatus of claim 4, wherein the mating fasteners comprise hook and loop fasteners.

6. The suspending apparatus as recited in claim 1, wherein the first shell is adapted to cover at least a portion of the edges of the second shell for enclosing at least a portion of the length of the residuum within the first shell and the second shell.

7. The suspending apparatus as recited in claim 1, wherein the second shell comprises an inner foam layer comprising a soft material, and an outer foam layer comprising a rigid material, wherein the outer foam layer is positioned adjacent to the inner foam layer.

8. An apparatus for post-amputation residuum maintenance for a below the knee amputation leaving a residuum having a medial femoral condyle defining a supracondylar space, the apparatus comprising:

an elongated posterior shell having a longitudinal axis and defining a hollow interior closed at a distal end, the posterior shell having an opening extending from a proximal end and adapted to receive a residuum into the hollow interior;

a pre-tibial shell having a longitudinal axis and arcuate in a cross-section taken transverse to the longitudinal axis, the pre-tibial shell adapted to be positioned adjacent to the residuum and configured to cover at least a portion of the opening of the posterior shell;

an elongated arcuate first suspension shell having a longitudinal axis and defining a first open interior channel, the first suspension shell adapted to receive at least a portion of the residuum and the posterior shell into the first open interior channel; and a flexible second suspension shell having a proximal end, a distal end, an inner surface defining a second open interior channel, and an outer surface, the second suspension shell including a wedge comprising a protrusion extending radially inwardly into the second open interior channel of the second shell from along a portion of the inner surface spaced from the proximal end and the distal end of the second shell, wherein the protrusion is elongated and includes a pair of major side surfaces projecting into the second open interior channel at an angle other than normal with respect to the inner surface of the second shell, the side surfaces joining at a common longitudinal ridge coaxial with a central longitudinal axis of the protrusion and extending partially circumferentially along the inner surface of the second shell, the second suspension shell configured to be received within the first suspension shell and adapted to cover the residuum adjacent to the knee forming a sleeve with the first suspension shell for surrounding the residuum and the posterior shell, wherein the wedge is adapted to bear against the residuum above the medial femoral condyle of the residuum such that the protrusion is received in the supracondylar space of the medial femoral condyle for suspending the residuum protection device.

9. The apparatus as recited in claim 8, further comprising a strap member secured to the second suspension shell, the strap member having a free distal end, and including a buckle at the other end, wherein the strap member is adapted to wrap around the first suspension shell and the second suspension shell compressing the suspension shells to a shape conforming to an outside surface of the combined suspension shells and the posterior shell.

10. The apparatus as recited in claim 9, wherein each of the ends of the strap member is configured to wrap in opposite directions around the suspension shells and the posterior shell, wherein the wrapped ends of the strap member are aligned.

11. The apparatus of claim 10, further comprising a pair of mating fasteners spaced on an outer surface of the free distal end of the strap member for securing the overlapping free distal end of the strap member.

12. The apparatus of claim 11, wherein the mating fasteners comprise hook and loop fasteners.

13. The apparatus as recited in claim 8, wherein the first suspension shell is adapted to cover at least a portion of the edges of the second suspension shell for enclosing at least a portion of the length of the residuum within the first suspension shell and the second suspension shell.

14. The apparatus as recited in claim 8, wherein the second suspension shell comprises an inner foam layer comprising a soft material, and an outer foam layer comprising a rigid material, wherein the outer foam layer is positioned adjacent to the inner foam layer.

* * * * *